United States Patent
Chen

(10) Patent No.: US 8,931,893 B2
(45) Date of Patent: Jan. 13, 2015

(54) MULTI-PURPOSE EYEGLASSES

(75) Inventor: Pen-Wei Chen, Tainan (TW)

(73) Assignee: Prohero Group Co., Ltd., Tainan (TW)

( * ) Notice: Subject to any disclaimer, the term of this patent is extended or adjusted under 35 U.S.C. 154(b) by 141 days.

(21) Appl. No.: 13/571,586

(22) Filed: Aug. 10, 2012

(65) Prior Publication Data

US 2014/0043581 A1 Feb. 13, 2014

(51) Int. Cl.
*G02C 9/00* (2006.01)
*G02C 7/08* (2006.01)

(52) U.S. Cl.
USPC ............ 351/47; 351/48; 351/57; 351/58

(58) Field of Classification Search
USPC ............. 351/44, 57, 58, 124, 47, 48
See application file for complete search history.

(56) References Cited

U.S. PATENT DOCUMENTS

2007/0024806 A1* 2/2007 Blanshay et al. ............... 351/62

* cited by examiner

*Primary Examiner* — Scott J Sugarman
*Assistant Examiner* — Mustak Choudhury
(74) *Attorney, Agent, or Firm* — Rosenberg, Klein & Lee

(57) ABSTRACT

A pair of multi-purpose eyeglasses is revealed. It has a pair of eyeglasses having a mounting stand provided on the upper end of a nose pad, the mounting stand having a buckling portion and positioning portion provided thereon; and an auxiliary lens frame having a buckling rod provided at the front end of a nose bridge connecting two lens holding subframes, the buckling rod being press-fitted and fixed into the buckling portion. The eyeglasses may he a pair of sports sunglasses or a pair of ski goggles. The eyeglasses and the auxiliary lens frame can be easily and quickly assembled with or disassembled from each other according to a user's intention.

15 Claims, 5 Drawing Sheets

MULTI-PURPOSE EYEGLASSES

BACKGROUND OF INVENTION

1. Field of the Invention

The present invention relates to a pair of multi-purpose eyeglasses, more particularly to a sports sunglasses with which an auxiliary lens frame can be assembled in a quick and detachable manner, so as to have both the functions of sports sunglasses and the auxiliary lens frame simultaneously by attaching the auxiliary lens frame on a mounting stand provided at the upper end of nose pad of the sunglasses.

2. Brief Description of the Prior Art

In view of social and economic prosperity, people gradually began to attach importance to leisure activities along with the implementation of the two-day weekends, and the societies began to advocate nature as well as outdoor leisure lifestyle. Prevailing of the leisure activities t only leads to the sightseeing attraction boom but also increases the opportunities for people to travel outside. Numerous myopes in the case of strong sunshine can only wear glasses for myopia in order to see things clearly. However, they cannot wear sunglasses simultaneously to avoid the possible eye-damage caused by UV light of strong sunshine. Therefore, incapability of simultaneous wearing of both glasses for myopia and sunglasses is inconvenient in the case of strong sunshine during egression.

In view of the disadvantages encountered in conventional eyeglasses structure, the inventor of the present invention hereby proposes a pair of multi-purpose eyeglasses according to the improvement and research conducted on conventional eyeglasses, so as to achieve better value of implementation.

SUMMARY OF INVENTION

The main object of the present invention is to provide a pair of multi-purpose eyeglasses, more particularly to a sports sunglasses with which an auxiliary lens can be quickly detachably assembled, and which can have both the functions of sports sunglasses and the auxiliary lens frame simultaneously by attaching the auxiliary lens frame on a mounting stand provided at the upper end of nose pad of the sunglasses.

In order to achieve the main object and effect of the multi-purpose eyeglasses, it mainly comprises an eyeglasses having a mounting stand provided on the upper end of the nose pad thereof, the mounting stand having a buckling portion provided thereon; and an auxiliary lens frame having a buckling rod provided at the front end of a nose bridge connecting two lens holding sub-frames. The buckling rod can be press-fitted and fixed into the buckling portion, so that the auxiliary lens frame cannot move back and forth. In this manner, the auxiliary lens frame can be easily and quickly assembled at the inside of the eyeglasses so as to allow users enjoying both functions of sports sunglasses as well as auxiliary lens frame simultaneously.

According to the multi-purpose eyeglasses of the present invention, the mounting stand is integrally formed and made from plastic material.

According to the multi-purpose eyeglasses of the present invention, a projection is provided at the lower end of the nose bridge of the attached frame for engaging with a positioning portion provided correspondingly on the mounting stand so that the auxiliary lens frame can be securely fixed in place.

According to a preferred embodiment of multi-purpose eyeglasses of the present invention, the auxiliary lens frame is a frame with myopia lenses.

According to a preferred embodiment of multi-purpose eyeglasses of the present invention, the eyeglasses are sports sunglasses. Further, According to another preferred embodiment, the eyeglasses are ski goggles.

According to still another preferred embodiment of multi-purpose eyeglasses of the present invention, snap fit arms are provided downwardly in ramp manner at both sides of the mounting stand, and snap fit recesses are respectively provided at the lower end face of the mounting stand and the ends inside both snap fit arms for engaging securely with the corresponding ridges provided at the front ends of the nose pad of the ski goggles.

Summing up above, the assembly structure for eyeglasses attached frame of the present invention has the advantages in its overall implementation as below.

1. As the auxiliary lens frame is fixed on the mounting stand in buckling mode, users can easily and quickly assemble and disassemble the attached frame so as to cope with different environmental demand. Therefore, it is easy and convenient muse, and the freedom of implementation is large.

2. The multi-purpose eyeglasses of the present invention can be adaptable to sports sunglasses and ski goggles. Users with myopia can enjoy simultaneously both functions of sports sunglasses and glasses for myopia in outdoor activities.

DETAILED DESCRIPTION OF PREFERRED EMBODIMENTS

The objects, the technical contents and the expected effect of the present invention will become more apparent from the detailed description of the preferred embodiments in conjunction with the accompanying drawings.

Figure 1:
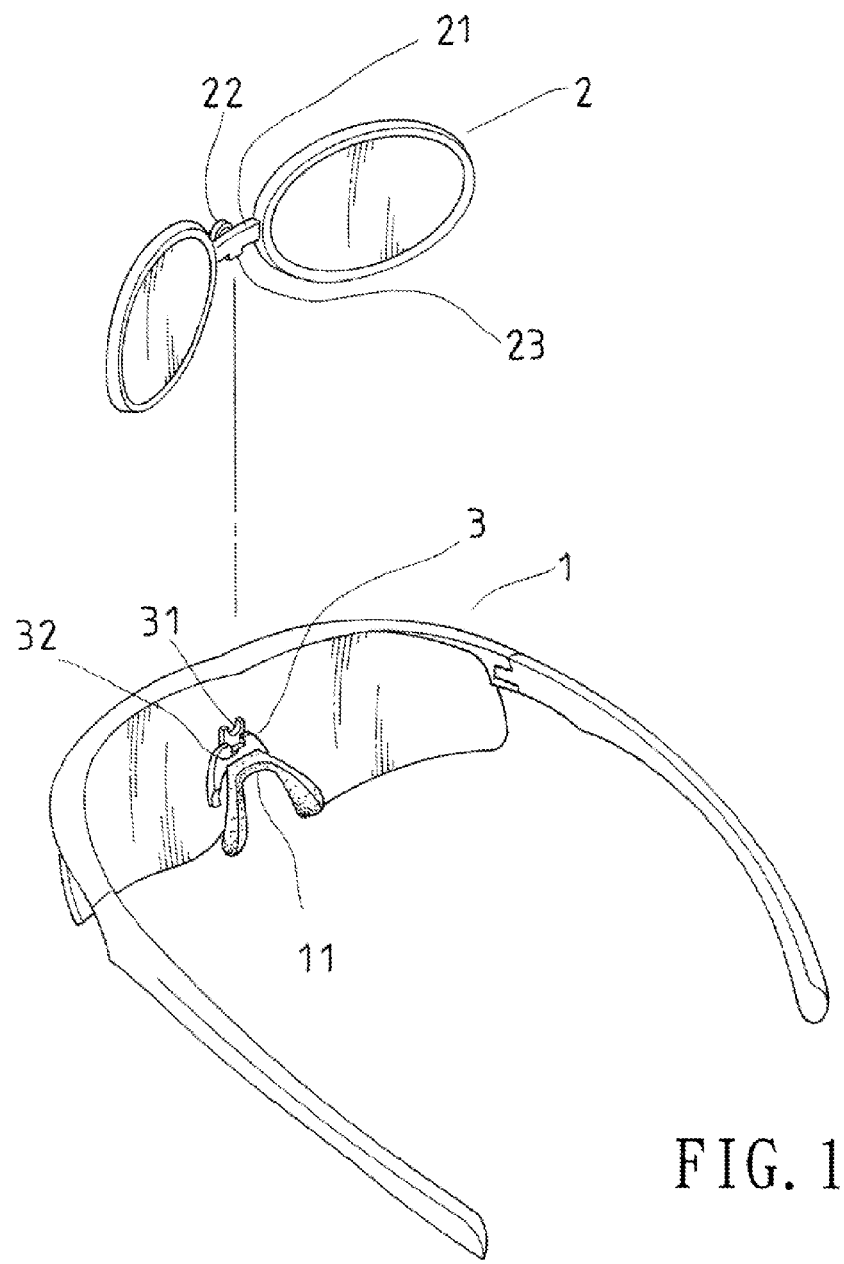
FIG. 1 is a perspective exploded view showing the first embodiment of the present invention.
Figure 2:
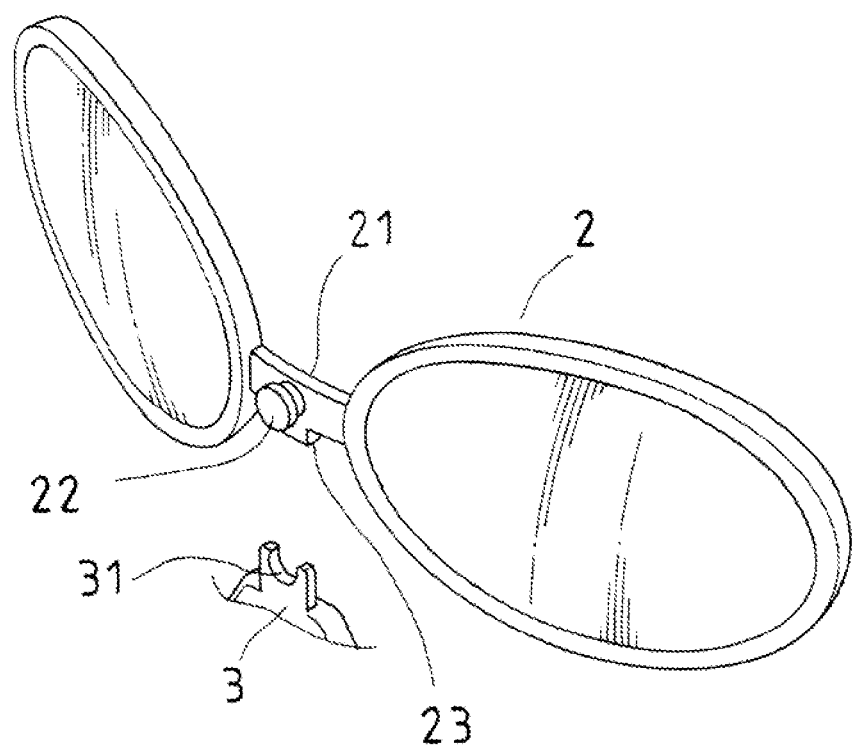
FIG. 2 is a partially enlarged perspective view showing the first embodiment of the present invention.
Figure 3:
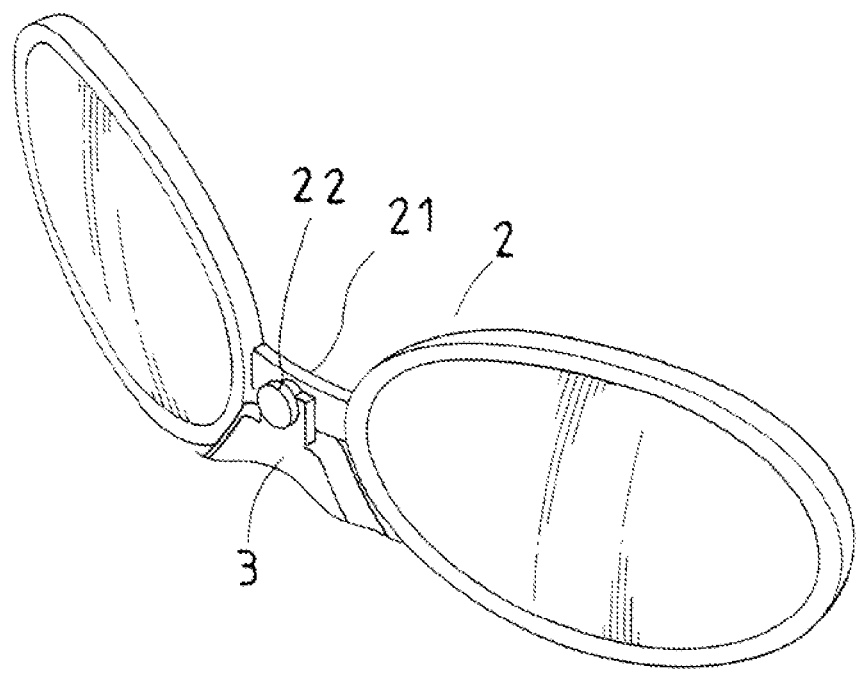
FIG. 3 is a schematic view showing the first embodiment of the present invention in assembled state.

FIG. 1 is a exploded perspective view showing a first embodiment of the multi-purpose eyeglasses of the present invention; FIG. 2 is a partially enlarged perspective view and FIG. 3 is a schematic view showing the first embodiment of the multi-purpose eyeglasses of the present invention in an assembled state. Referring to FIGS. 1 to 3, the multi-purpose eyeglasses of the present invention comprises an eyeglasses (1), which in a preferred embodiment of the present invention is a pair of sports sunglasses, having a mounting stand (3) provided at the upper end of the nose pad (11) thereof the mounting stand (3) being integrally formed and made from plastic material and being inserted in the upper end of the nose pad (11) of the eyeglasses (1), a buckling portion (31) being provided on the mounting stand (3); and an auxiliary lens frame (2), which in a preferred embodiment of the present invention is a frame with myopia lenses, having a buckling rod (22) provided at the front end of a nose bridge (21) connecting the two lens holding sub-frames, the buckling rod (22) being press-fitted and fixed into the buckling, portion (31) in such a manner that the attached frame (2) is unable to move back and forth. In this manner, the frame for myopia can be easily and quickly assembled at the inside or the sports sunglasses so as to allow users to enjoy simultaneously both functions of sports sunglasses as well, as frame for myopia.

According to the auxiliary lens of the present invention, a projection (23) is provided at the lower end face of the nose bridge (21) of the attached frame (2) for engaging with a positioning portion (32) provided correspondingly on the mounting stand so that the attached frame can be securely fixed in place.

Figure 4:
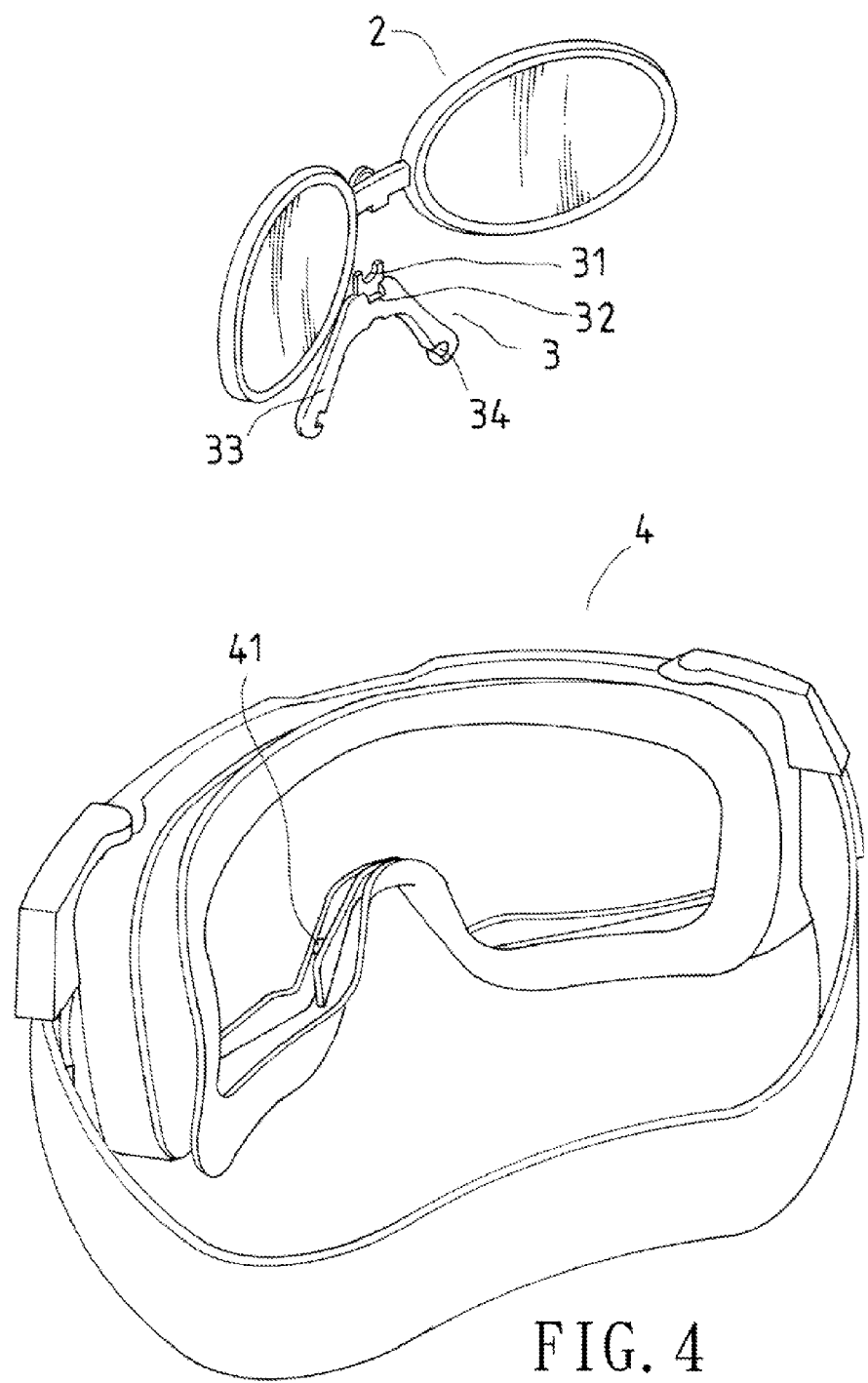
FIG. 4 is a perspective exploded view showing the second embodiment of the present invention.
Figure 5:
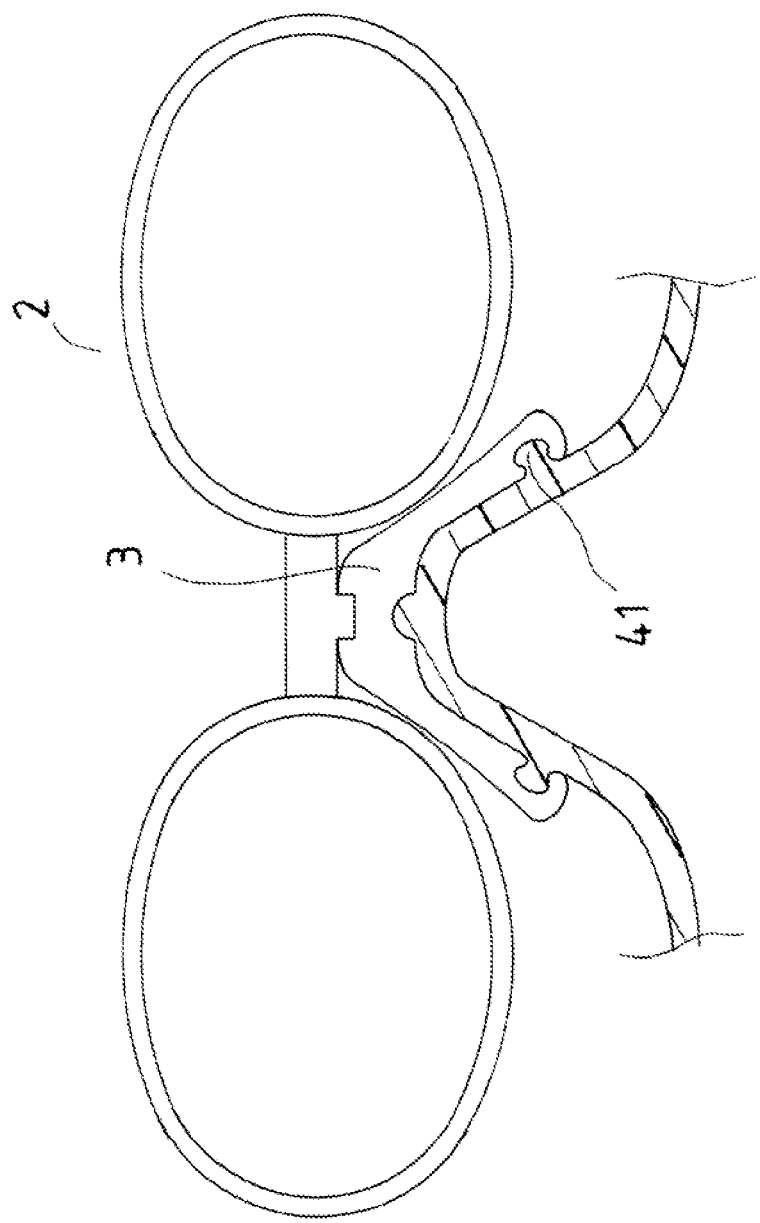
FIG. 5 is a schematic view showing the second embodiment of the present invention in assembled state.

FIGS. 4 and 5 are respectively an exploded perspective view and a partially enlarged assembled schematic view of the second embodiment of the present invention. The second embodiment is substantially the same as the first embodiment, except the difference in that the pair of eyeglasses (1) is a pair of ski goggles (4). Each of snap fit arms (33) is extended in a downward slopping direction from both sides of the mounting stand (3), and snap fit recesses (34) are respectively provided at the lower end face of the mounting stand (3) and the ends inside both snap fit arms (33) for engaging securely with the corresponding ridges (41) provided at the front ends of the nose pad of the ski goggles (4). In this manner, the eyeglasses simultaneously have both functions of the ski goggles and the glasses for myopia.

Configuring in this manner, the multi-purpose eyeglasses according to the present invention has its attached frame to be fixed on the mounting stand in buckling mode, so users can easily and quickly assemble and disassemble the auxiliary lens holding frame so as to cope with different environmental demands. Therefore, it is very simple and convenient in its overall implementation.

It is to be understood that the abovementioned embodiments and the drawings are not intended to limit the structural aspect or dimensions of the present invention. Appropriate variations or modifications conducted by person having general knowledge in the art are still regarded to be within the scope of the invention.

What is claimed is:

1. A pair of multi-purpose eyeglasses, comprising:
   eyeglasses having an outer lens portion disposed forward of a mounting stand provided on an upper end of a nose pad thereof, said mounting stand having a buckling portion projecting forward from a positioning portion toward said outer lens portion; and
   an auxiliary lens frame detachably coupled to said eyeglasses, said auxiliary lens frame having a buckling rod and a projection extending in mutually transverse directions from a nose bridge connecting two lens holding sub-frames, said buckling rod being press-fitted and fixed in cradled manner into said buckling portion and said projection concurrently engaging said positioning portion.

2. A pair of multi-purpose eyeglasses as claimed in claim 1, wherein said projection is provided at the lower end of the nose bridge of said auxiliary lens frame for engaging with said positioning portion provided correspondingly on said mounting stand.

3. A pair of multi-purpose eyeglasses as claimed in claim 2, wherein said eyeglasses is a pair of sports sunglasses.

4. A pair of multi-purpose eyeglasses as claimed in claim 2, wherein said auxiliary lens frame is a frame with myopia lenses.

5. A pair of multi-purpose eyeglasses as claimed in claim 2, wherein said mounting stand is made from plastic material.

6. A pair of multi-purpose eyeglasses as claimed in claim 2, wherein said eyeglasses is a pair of ski goggles.

7. A pair of multi-purpose eyeglasses as claimed in claim 6, wherein a snap fit arm is extended in a downward slopping direction from both sides of said mounting stand.

8. A pair of multi-purpose eyeglasses as claimed in claim 7, wherein snap fit recesses are respectively provided at the lower end face of said mounting stand and the ends inside both said snap fit arms for engaging securely with corresponding ridges provided at the front ends of the nose pad of the ski goggles.

9. A pair of multi-purpose eyeglasses as claimed in claim 1, wherein said eyeglasses is a pair of sports sunglasses.

10. A pair of multi-purpose eyeglasses as claimed in claim 1, wherein said auxiliary lens frame is a frame with myopia lenses.

11. A pair of multi-purpose eyeglasses as claimed in claim 1, wherein said mounting stand is made from plastic material.

12. A pair of multi-purpose eyeglasses as claimed in claim 1, wherein said eyeglasses is a pair of ski goggles.

13. A pair of multi-purpose eyeglasses as claimed in claim 12, wherein a snap fit arm is extended in a downward slopping direction from both sides of said mounting stand.

14. A pair of multi-purpose eyeglasses as claimed in claim 13, wherein snap fit recesses are respectively provided at the lower end face of said mounting stand and the ends inside both said snap fit arms for engaging securely with corresponding ridges provided at the front ends of the nose pad of the ski goggles.

15. A pair of multi-purpose eyeglasses as claimed in claim 1, wherein said buckling rod of said auxiliary lens frame includes a cylindrical base portion projecting forward from said nose bridge to terminate at an increased diameter end portion, said base portion of said buckling rod being cradled in said buckling portion, said end portion bearing against a forward side of said buckling portion to stop said auxiliary lens frame against rearward displacement away from said outer lens portion of said eyeglasses.

* * * * *